United States Patent
Min et al.

(10) Patent No.: US 8,923,965 B2
(45) Date of Patent: Dec. 30, 2014

(54) SYSTEMS AND METHODS FOR OPTIMIZING AV/VV PACING DELAYS USING COMBINED IEGM/IMPEDANCE-BASED TECHNIQUES FOR USE WITH IMPLANTABLE MEDICAL DEVICES

(75) Inventors: Xiaoyi Min, Thousand Oaks, CA (US); Gene A. Bornzin, Simi Valley, CA (US); Martin Cholette, Acton, CA (US); Kyungmoo Ryu, Palmdale, CA (US); Catherine Tan, North Hollywood, CA (US)

(73) Assignee: Pacesetter, Inc., Sylmar, CA (US)

( * ) Notice: Subject to any disclaimer, the term of this patent is extended or adjusted under 35 U.S.C. 154(b) by 802 days.

(21) Appl. No.: 12/976,322

(22) Filed: Dec. 22, 2010

(65) Prior Publication Data
US 2012/0165892 A1 Jun. 28, 2012

(51) Int. Cl.
A61B 1/00 (2006.01)
A61N 1/365 (2006.01)

(52) U.S. Cl.
CPC ............. *A61N 1/36585* (2013.01); *A61N 1/365* (2013.01); *A61N 1/36521* (2013.01)
USPC ............................... 607/25; 607/9

(58) Field of Classification Search
USPC ................................. 607/9, 17–18, 14, 24–25
See application file for complete search history.

(56) References Cited

U.S. PATENT DOCUMENTS

| | | | |
|---|---|---|---|
| 7,248,925 B2 | 7/2007 | Bruhns et al. | |
| 7,590,446 B1 | 9/2009 | Min et al. | |
| 2009/0287267 A1* | 11/2009 | Wenzel et al. | 607/9 |
| 2009/0299423 A1* | 12/2009 | Min | 607/9 |
| 2012/0150253 A1* | 6/2012 | Burnes et al. | 607/18 |

OTHER PUBLICATIONS

Baker II, et al., "Acute Evaluation of Programmer-Guided AV/PV and VV Delay Optimization Comparing an IEGM Method and Echocardiogram for Cardiac Resynchronizaion Therapy in Heart Failure Patients and Dual Chamber ICD Implants." J Cardiovasc Electrophysiol. Feb. 2007; 18(2):185-91.
Zuber et al., "Comparison of Different Approaches for Optimization of Atrioventricular and Interventricular Delay in Biventricular Pacing." Europace (2008) 10, 367-373.

* cited by examiner

*Primary Examiner* — Catherine Voorhees

(57) ABSTRACT

Systems and methods are provided wherein intracardiac electrogram (IEGM) signals are used to determine a set of preliminary optimized atrioventricular (AV/PV) and interventricular (VV) pacing delays. In one example, the preliminary optimized AV/VV pacing delays are used as a starting point for further optimization based on impedance signals such as impedance signals detected between a superior vena cava (SVC) coil electrode and a device housing electrode, which are influenced by changes in stroke volume within the patient. Ventricular pacing is thereafter delivered using the AV/VV pacing delays optimized via impedance. In another example, parameters derived from IEGM signals are used to limit the scope of an impedance-based optimization search to reduce the number of pacing tests needed during impedance-based optimization. Biventricular and multi-site left ventricular (MSLV) examples are described.

5 Claims, 10 Drawing Sheets

SYSTEMS AND METHODS FOR OPTIMIZING AV/VV PACING DELAYS USING COMBINED IEGM/IMPEDANCE-BASED TECHNIQUES FOR USE WITH IMPLANTABLE MEDICAL DEVICES

FIELD OF THE INVENTION

The invention generally relates to implantable cardiac stimulation devices such as pacemakers, implantable cardioverter-defibrillators (ICDs) and cardiac resynchronization therapy (CRT) devices and, in particular, to techniques for determining preferred or optimal atrioventricular (AV/PV) and interventricular (VV) pacing delays for use by such devices.

BACKGROUND OF THE INVENTION

Clinical studies related to cardiac pacing have shown that an optimal atrio-ventricular pacing delay (e.g., AV delay or PV delay) and/or an optimal interventricular pacing delay (e.g., VV delay) can improve cardiac performance. However, such optimal delays depend on a variety of factors that may vary over time. Thus, what is "optimal" may vary over time. An optimization of AV/PV pacing delay and/or VV pacing delay may be performed at implantation and, in some cases, a re-optimization may be performed during a follow-up consultation. While optimization procedures are beneficial, the benefits may not last due to changes in various factors related to device and/or cardiac function. Accordingly, techniques have been developed for periodically re-optimizing pacing delays. Periodic re-optimization is particularly important when providing CRT. Briefly, CRT seeks to normalize asynchronous cardiac electrical activation and resultant asynchronous contractions associated with heart failure by delivering synchronized pacing stimulus to both ventricles. The stimulus is synchronized so as to improve overall cardiac function. This may have the additional beneficial effect of reducing the susceptibility to life-threatening tachyarrhythmias. Pacemakers and ICDs can be equipped to deliver CRT. Standalone CRT devices can also be provided for implant within patients. By periodically re-optimizing CRT, its operation can be adjusted to respond to the needs of the patient.

The following patents and patent applications set forth various systems and methods for allowing a pacemaker, ICD, CRT device or other cardiac rhythm management (CRM) device to determine and/or adjust AV/PV/VV pacing delays so as to help maintain the pacing delays at preferred or optimal values: U.S. Pat. No. 7,590,446; U.S. Published Patent Application 2009/0299423A1; U.S. patent application Ser. No. 11/952,743 (abandoned), filed Dec. 7, 2007, entitled "Systems and Methods for Determining Optimal Atrioventricular Pacing Delays using either Paced or Sensed Atrial Beats"; U.S. patent application Ser. No. 12/328,605, filed Dec. 4, 2008, issued as U.S. Pat. No. 8,442,634, entitled "Systems and Methods for Controlling Ventricular Pacing in Patients with Long Intra-Atrial Conduction Delays"; U.S. patent application Ser. No. 12/507,646, filed Jul. 22, 2009, issued as U.S. Pat. No. 8,265,755, of Min et al. entitled "Systems and Methods for Optimizing Ventricular Pacing Delays for use with Multi-Pole Leads"; U.S. patent application Ser. No. 12/639,881 (pending), filed Dec. 16, 2009, of Min et al., entitled "Systems and Methods for Determining Ventricular Pacing Sites for use with Multi-Pole Leads"; U.S. patent application Ser. No. 12/604,280, filed Oct. 22, 2009, issued as U.S. Pat. No. 8,145,311, of Min et al., entitled "Systems and Methods for Determining Optimal Electrode Pairs for use in Biventricular Pacing using Multi-Pole Ventricular Leads"; and U.S. patent application Ser. No. 12/957,142 (pending), filed Nov. 30, 2010, of Min, entitled "Systems and Methods for Determining Optimal Atrioventricular Pacing Delays based on Cardiomechanical Delays". See, also, U.S. Pat. No. 7,248,925, to Bruhns et al., entitled "System and Method for Determining Optimal Atrioventricular Delay based on Intrinsic Conduction Delays." At least some of the techniques are implemented within the QuickOpt™ systems of St. Jude Medical.

In particular, techniques were set forth within at least some of these patent documents for exploiting various inter-atrial and interventricular conduction delays observed within an intracardiac electrogram (IEGM) to determine preferred or optimal AV/PV/VV pacing delays. In at least some examples, the implanted device (or an external programming device in communication with the implanted device) performs a series of tests to determine intrinsic AV/PV and VV conduction delays from which preferred pacing delays are determined. In particular, an "A sense" test is performed to detect intra-atrial conduction delays from which preferred IEGM-based AV/PV pacing delays are determined. A "V sense" test is performed to detect intrinsic ventricular events from which an intrinsic interventricular conduction delay ($\Delta$) is determined. An "RV pace" test and a separate "LV pace" test are performed to detect paced interventricular conduction delays (IVCD_RL and IVCD_LR, respectively) from which an intrinsic interventricular correction term ($\epsilon$) is determined. The optimal IEGM-based VV delay is then set based on $\Delta$ and $\epsilon$. In some examples, a pacing latency correction term is applied during the determination of PV. Other examples extend these techniques for use with multi-site LV (MSLV) pacing.

Although these "IEGM-based" techniques are useful, there remains room for further improvement, particularly in terms of the capability of the techniques to identify values for AV/PV/VV pacing delays that optimize or improve cardiac output or stroke volume. It is known that LV dP/dt is a good surrogate for contractility and stroke volume. It has been found that that certain features of impedance signals (Z) measured between the device housing (can) and an electrode in the superior vena cava (SVC) correlate closely with LV dP/dt, at least in animal test subjects. Hence, it would be desirable to exploit SVC-can Z signals or other appropriate Z signals to improve the optimization of pacing delays and it is to this end that aspects of the present invention are generally directed. It would be particularly desirable to provide techniques that allow for Z signals to be exploited for optimization that do not require a large number of optimization tests and it is to this end that some particular aspects of the invention are directed.

SUMMARY OF THE INVENTION

In an exemplary embodiment, a method is provided for controlling ventricular pacing within a patient for use by an implantable medical device. Briefly, IEGM signals are detected within the patient using the electrodes and preliminary optimized AV/PV and VV pacing delays are determined based on the IEGM signals, such as by using the aforementioned IEGM-based QuickOpt techniques. These IEGM-based values are used as a starting point for further optimization based on impedance (Z) signals obtained along a vector wherein Z values are influenced by stroke volume. In one example, a transthoracic impedance signal is detected along an SVC-can vector between an SVC coil electrode and a device housing electrode and then IEGM-based AV/VV pacing delays are adjusted or further optimized using the impedance signal to yield impedance-based AV and VV pacing delays. Other impedance vectors can be used, such as RV coil-can. In general, any impedance vector that offers a good surrogate for stroke volume can be used. Ventricular pacing is thereafter delivered or otherwise controlled using the impedance-based AV/VV pacing delays. These techniques are generally referred to herein as a "hybrid" techniques since the techniques combine IEGM-based optimization with Z-based optimization.

In an illustrative embodiment of the hybrid technique, the techniques are applied for use with biventricular CRT pacing in an effort maximize cardiac output and/or stroke volume. A sense and V sense tests are performed to determine values for intrinsic conduction delays (AR and PR) within the patient and to determine a value for an intrinsic interventricular conduction delay ($\Delta$). RV pace and LV pace tests are performed to determine paced interventricular conduction delays (IVCD_RL and IVCD_LR) from which an intrinsic interventricular correction term ($\epsilon$) is determined using $\epsilon$=IVCD_LR−IVCD_RL. Then, an IEGM-based PV delay is set using IEGM_PV=IACD+$\delta$−$\theta$, where $\delta$ is an offset value and $\theta$ is a pacing latency correction term. An IEGM-based AV delay is set using IEGM_AV=IEGM_PV+dPA, where dPA=AR−PR. An IEGM-based VV delay is set using IEGM_VV=$\alpha$($\Delta$+$\epsilon$) where $\alpha$ is set to 0.5. Alternatively, this equation may be represented as IEGM_VV=0.5 (Vsense+LVpace−RVpace), where Vsense, LVpace and RVpace generally represent the outputs of the corresponding V sense, LV pace and RV pace tests.

The IEGM_AV and IEGM_VV values are then used as starting points for further optimization based on impedance values obtained along suitable vectors. In one example, a full grid search pattern is specified that encompasses the IEGM_AV and IEGM_VV values, such as a 4×4 grid is set based on: IEGM_AV±2A; IEGM_AV±A; IEGM_VV±A; and IEGM_VV±2A, where A is set to 20 milliseconds (ms) or other suitable grid spacing parameter. Then, for each combination of AV and VV delays within the search pattern, the device delivers test pacing pulses while measuring impedance to determine corresponding values for maximum Z (Zmax) and/or the maximum rate of change of Z (dZ/dtmax.) The device then identifies particular values for AV and VV that maximize Zmax and/or dZ/dtmax. These pacing delay values are referred to herein as AV_Z and VV_Z, since they are optimized based on Z rather than on the IEGM. Note that optimal PV delays are obtained directly from the IEGM (i.e. IEGM_PV) and are not further optimized based on Z values.

Biventricular pacing is then delivered using AV_Z and VV_Z so as to gain the benefit of the Z-based optimization to achieve improved cardiac output and stroke volume within the patient. In this regard, it is believed that pacing delay values that generally improve Zmax and/or dZ/dtmax along appropriate vectors also serve to generally improve LV dP/dtmax and likewise serve to generally improve cardiac output and stroke volume. Note that the overall procedure may be applied to periodically re-adjust the values of AV_Z and VV_Z based on the changing characteristics of the heart of the patient so as to keep the values at or near optimal values for maximizing cardiac output and stroke volume within the patient. Note also that by employing an impedance-based search that uses IEGM_AV and IEGM_VV values as starting points, the number of combinations of delay AV/VV values that need to be tested while measuring impedance can be reduced significantly as compared to grid search schemes that might otherwise test all permissible AV/VV delays.

In another illustrative embodiment, similar "hybrid" optimization techniques are applied for use with MSLV pacing rather than biventricular pacing. A significant reduction in the number of combinations of AV/VV delay values that need to be tested can likewise be achieved. In an alternative "direct" optimization technique, rather than determining the IEGM_AV and IEGM_VV values and then performing a full grid search based on those values, the system uses values derived from IEGM signals to set the parameters for a direct Z-based optimization search. In one particular example of the direct technique, the ranges of AV/VV values to be tested are limited based on parameters derived from A sense, V sense, LV pace and RV pace tests.

Note that, although impedance is used in the examples described herein, other generally equivalent electrical values or parameters can instead be used where appropriate, such as immittance, conductance, or admittance. Hence, the term "impedance," as it is used herein, broadly encompasses impedance and any equivalent electrical value or parameter.

System and method implementations of various exemplary techniques are presented herein.

BRIEF DESCRIPTION OF THE DRAWINGS

Features and advantages of the described implementations can be more readily understood by reference to the following description taken in conjunction with the accompanying drawings.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable Systems

Figure 1:
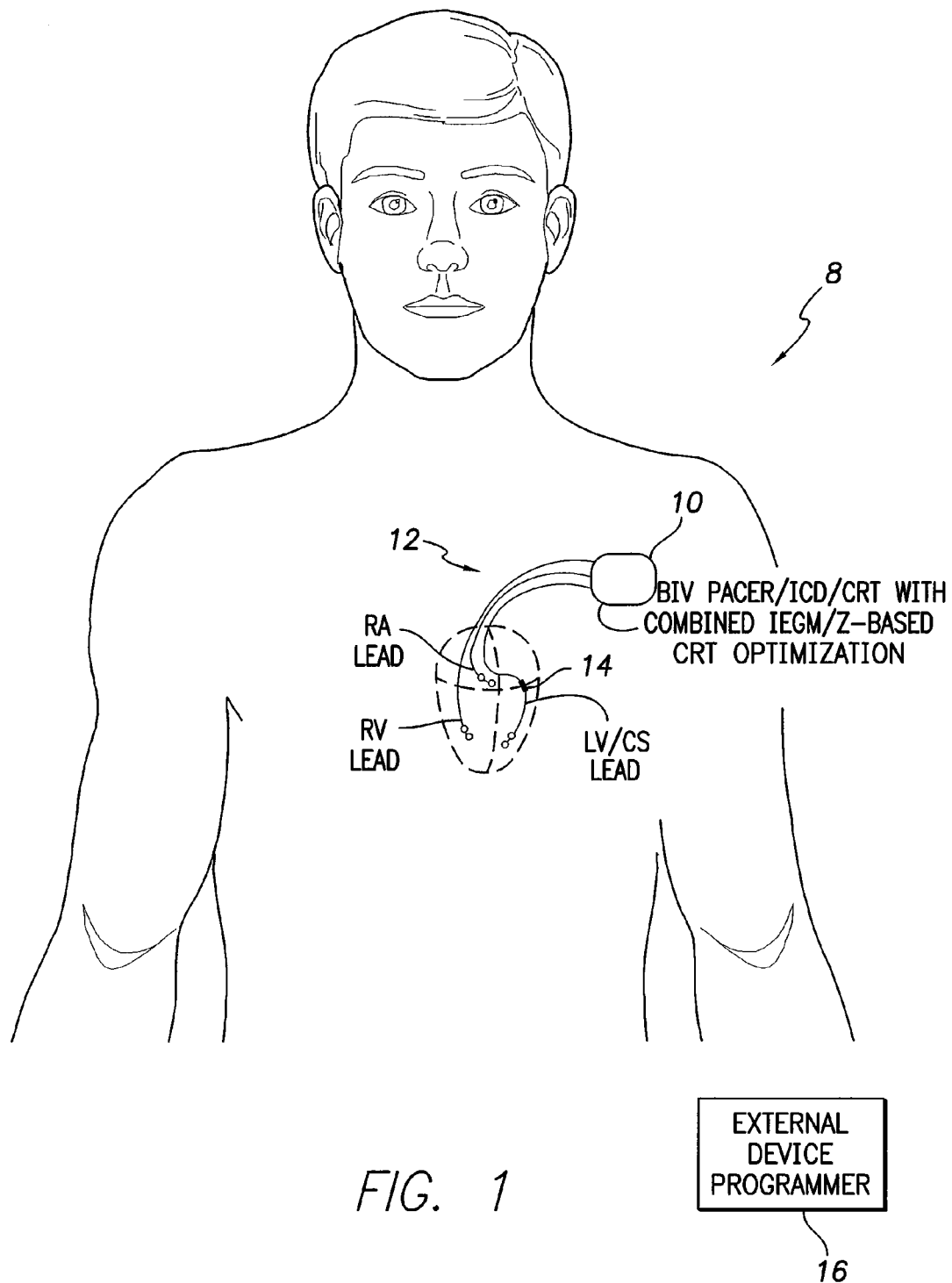
FIG. 1 illustrates pertinent components of an implantable medical system having a pacemaker, ICD or CRT device capable of optimizing AV/VV pacing delays using combined IEGM/impedance-based optimization techniques for use with biventricular pacing.

FIG. 1 illustrates an implantable medical system 8 capable of performing rapid optimization of biventricular pacing parameters, such as AV/VV pacing delays, by using a combination of IEGM signals and suitable impedance (Z) measurements. Biventricular system 8 includes a pacer/ICD/CRT device 10 or other cardiac rhythm management device equipped with one or more bipolar cardiac sensing/pacing leads 12 implanted on or within the heart of the patient, including a bipolar LV lead implanted via the coronary sinus (CS). The LV lead includes an SVC coil 14 for use in measuring an SVC coil-can impedance signal for Z-based AV/VV optimization. It should be understood that additional or alternative electrodes, sensors or other devices could be connected to the various leads. The system of FIG. 1 is generally capable of performing either or both of the aforementioned hybrid and direct optimization techniques, as well other suitable optimization techniques.

Figure 2:
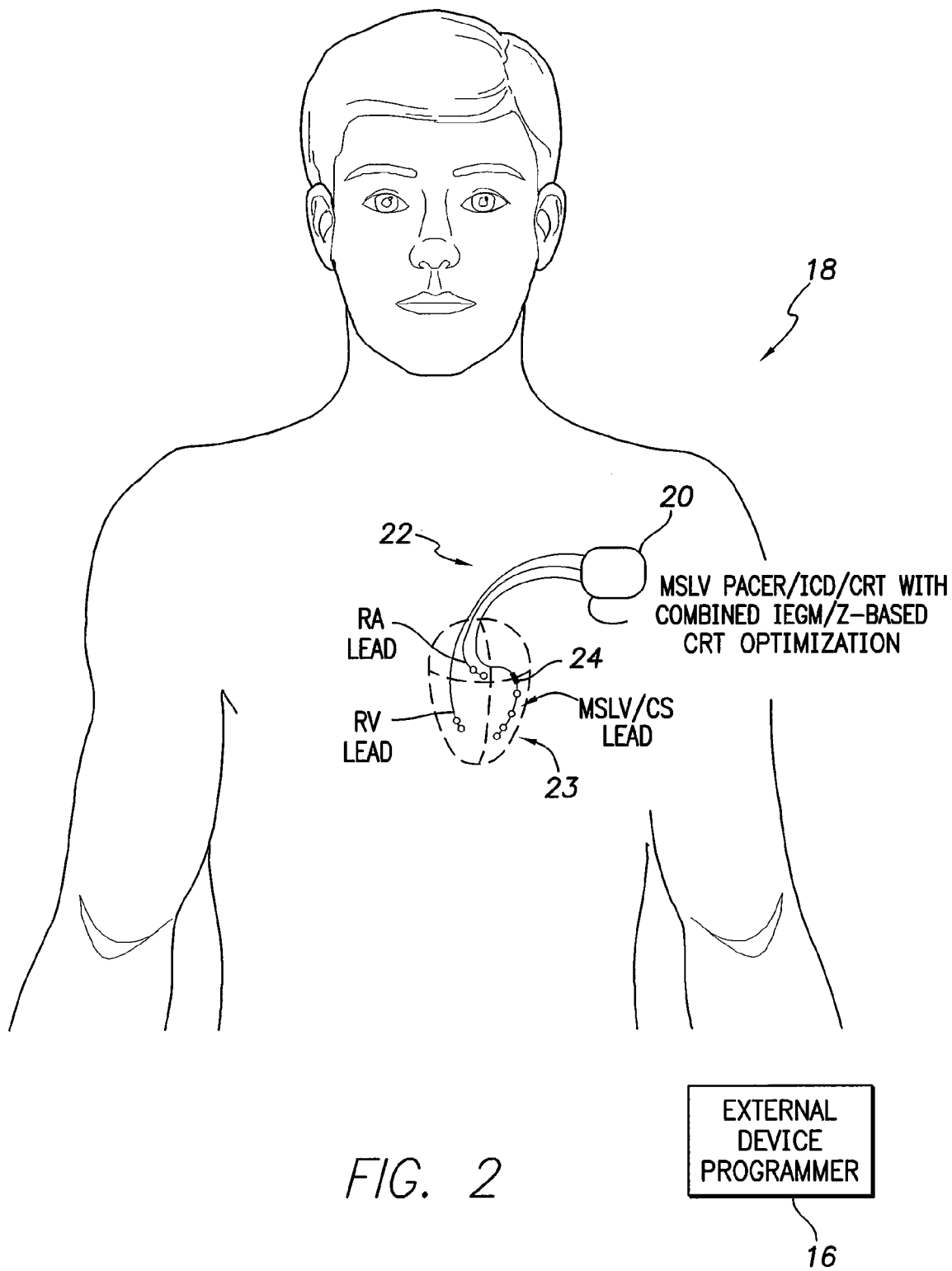
FIG. 2 illustrates pertinent components of an implantable medical system similar to that of FIG. 1 but equipped with a quadrapole LV lead for MSLV pacing.

For the sake of completeness, an MSLV version of FIG. 1 is also provided. Briefly, FIG. 2 illustrates an alternative implantable medical system 18 capable of performing rapid optimization of MSLV pacing parameters, such as AV/VVn pacing delays. System 18 includes an MSLV pacer/ICD/CRT device 20 equipped with a set of leads 22, including a quad-rapolar MSLV lead implanted via the CS, which includes an SVC coil 24. To illustrate the multi-pole configuration of the LV lead, a set of electrodes 23 is shown distributed along the LV lead. The RV and RA leads are each shown as having a bipolar tip/ring electrode pair, though each of those leads may include additional multi-polar electrodes, as well such as coil electrodes. See FIG. 8 for a more complete and accurate illustration of various exemplary leads. As with the system of FIG. 1, the system of FIG. 2 is likewise capable of performing either or both of the aforementioned hybrid and direct optimization techniques, as well other suitable optimization techniques.

Herein, for brevity, the pacer/ICD/CRT devices of FIGS. 1 and 2 are referred to simply as a "pacer/ICD." In some implementations, the pacer/ICD itself performs the CRT optimization based on IEGM signals and impedance measurements obtained using its leads. In other implementations, the device transmits features of the IEGM signals, as well as impedance measurements, to an external device programmer 16 that performs the optimization. That is, the device programmer determines optimal AV/VV pacing parameters, which are then programmed into the pacer/ICD via telemetry. Other external devices might instead be used to perform the optimization, such as bedside monitors or the like. In some embodiments, the device programmer or bedside monitor is directly networked with a centralized computing system. The centralized system may include such systems as Merlin.Net of St. Jude Medical, which may be used in conjunction with bedside monitors or similar devices such as the HouseCall™ remote monitoring system or the Merlin@home systems, also of St. Jude Medical.

In the following examples, it is assumed that the pacer/ICD performs the AV/VV optimization using on-board components. An embodiment where the external programmer performs the optimization is described below with reference to FIG. 10.

Hybrid Optimization Techniques Using IEGM and Z Parameters

Figure 3:
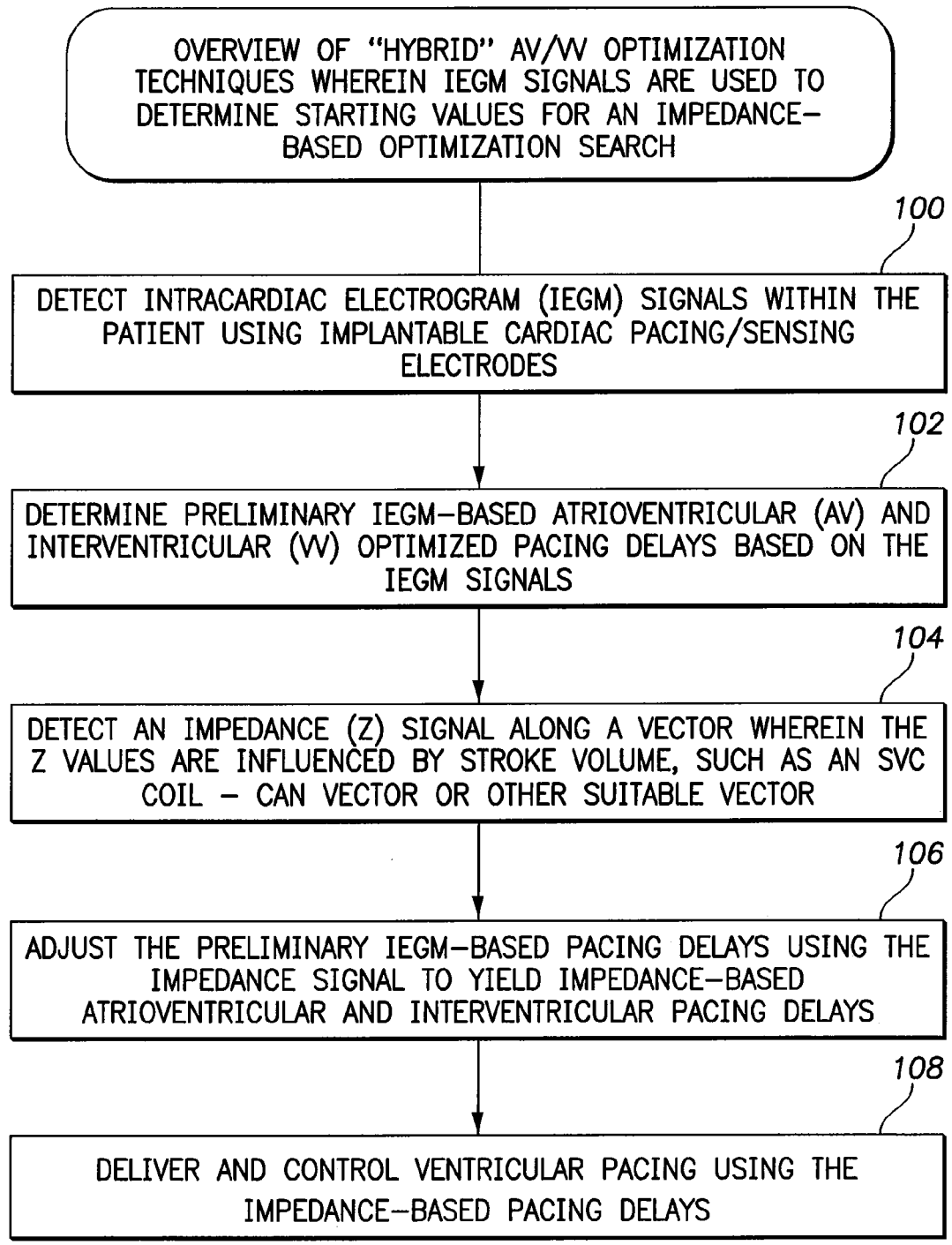
FIG. 3 provides an overview of the hybrid optimization techniques that may be performed by the systems of FIGS. 1 and 2, wherein IEGM-based optimization is used to determine starting values for further Z-based optimization.

FIG. 3 broadly summarizes the hybrid technique wherein IEGM signals are used to determine preliminary values for AV/VV for use as starting points of a subsequent impedance-based optimization search. These hybrid techniques may be exploited by the pacer/ICDs of FIGS. 1 and 2 or other suitably-equipped systems. Beginning at step 100, the pacer/ICD detects IEGM signals within the patient using implantable cardiac pacing/sensing electrodes. At step 102, the device determines preliminary IEGM-based AV and VV optimized pacing delays based on the IEGM signals using, for example, the aforementioned QuickOpt techniques. At step 104, the device then detects a transthoracic impedance Z signal along a vector between an SVC electrode (such as SVC coil electrode 14 of FIG. 1) and a device housing electrode or by using any other suitable impedance vector such as RV coil-CAN. Additionally, cardiogenic impedance (CI) can be derived such as by using RV bipolar and LV bipolar configurations. In general, any impedance method or vector that provides a good surrogate for stroke volume can be used. For example, RV ring to SVC for injecting current can create and spherical iso-potential surfaces from RV ring, so that LV electrodes can sense motion of the heart consistently by unipolar LV sensing and the sum of the potential changes can be used to estimate the stroke volume. Other vectors include injecting current between the RV Coil or RV ring to Can while sensing voltage between RA ring or SVC coil to Can to estimate impedance for estimating stroke volume.

At step 106, the device adjusts the IEGM-based pacing delays based on the impedance signal to yield impedance-based AV/VV pacing delays, such as by using the IEGM-based delays as starting points for a Z-based AV/VV optimization search. In other words, Z-based optimization is used to refine or confirm the initial IEGM-based optimization in an effort to further improve cardiac output and stroke volume within the patient. This technique wherein Z is used to refine or confirm the initial IEGM-based optimization may be regarded as being a "closed loop" technique since the IEGM-based optimization does not necessarily give any direct clinically-related measures whereas Z does. Hence, the Z values "close the loop" back to clinically relevant values. At step 108, the device then controls the delivery of ventricular pacing using the adjusted optimized pacing AV/VV pacing delays, such as by controlling CRT using those delays.

Figure 4:
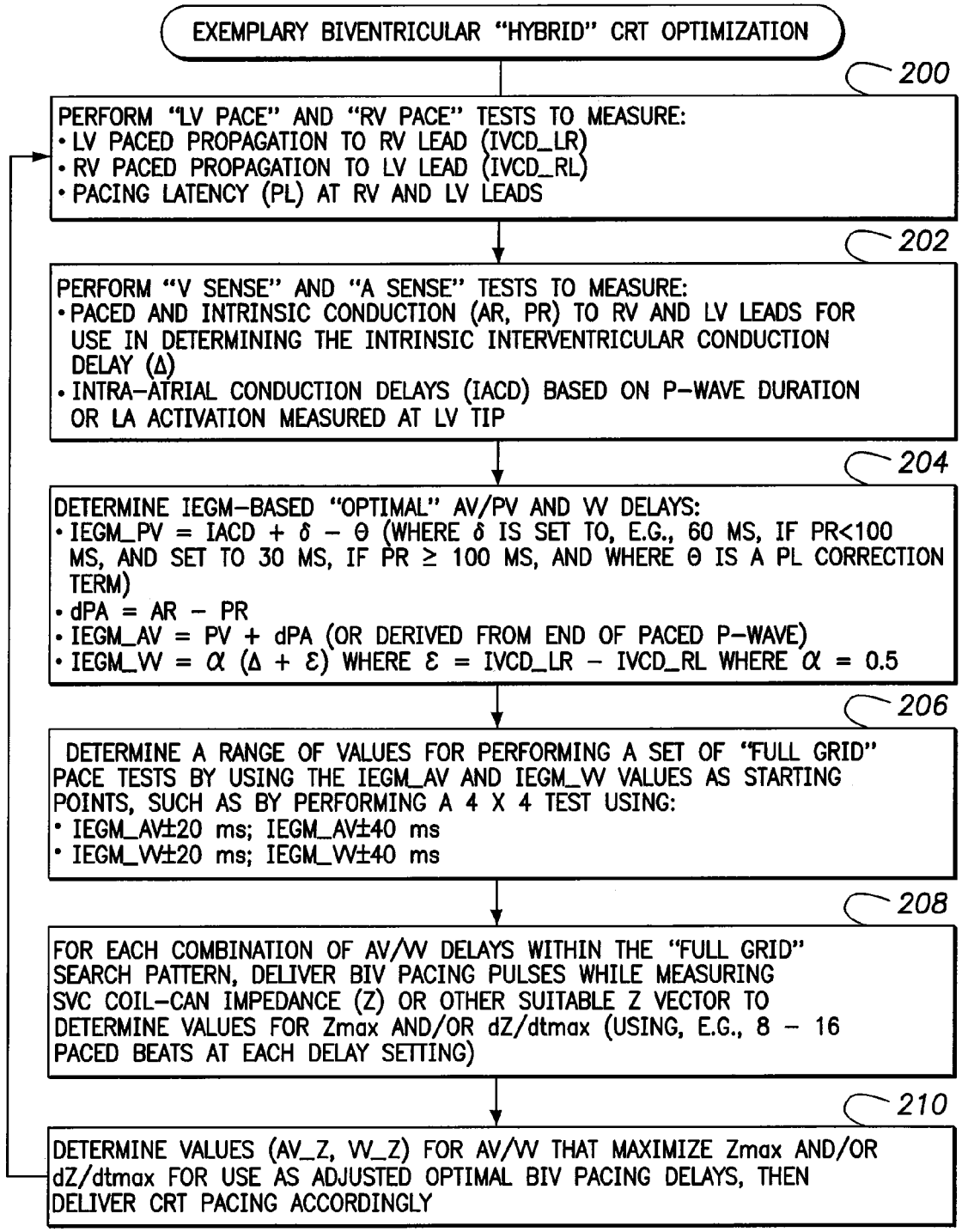
FIG. 4 illustrates an exemplary biventricular implementation of the hybrid technique of FIG. 3.

FIG. 4 illustrates a more detailed example of the hybrid technique. Beginning at step 200, the device performs "LV pace" and "RV pace" tests to measure: (a) LV paced propagation to RV lead (IVCD_LR); (b) RV paced propagation to LV lead (IVCD_RL); and (3) pacing latency at RV and LV leads. More specifically, one or more LV pace tests are performed to detect a pacing latency (PL) value based on LV pacing pulses delivered using the LV tip/ring electrode pair. In one example, an LV pulse (LV-pulse) is delivered and then the evoked response (ER) is detected using the LV tip/ring. The time delay from the LV pulse to the peak of ER is the pacing latency PL for the LV. The pacing delay from the LV to the RV is denoted IVCD_LR. Likewise, one or more RV pace tests are performed to detect the pacing delay from the RV tip/ring electrode pair to the LV (IVCD_RL), as well as the pacing latency at the RV. LV and RV pace tests are described in U.S. patent application Ser. No. 12/604,280, which is incorporated herein by reference.

At step 202, the device performs "V sense" and "A sense" tests to measure: (a) paced and intrinsic conduction (AR, PR) to RV and LV leads for use in determining the intrinsic interventricular conduction delay (Δ) and (b) the intra-atrial conduction delay (IACD) based on P-wave duration or LA activation measured at LV tip. That is, the V sense test is performed to detect an amount of intrinsic electrical separation ($\Delta$) between the RV tip/ring pair and the LV tip/ring pair. The V sense test is also described in U.S. patent application Ser. No. 12/604,280. The A sense test is performed to determine or estimate the IACD. The IACD is described in U.S. patent application Ser. No. 12/132,563, which is also incorporated by reference. Note that AR can also be referred to as AE; PR can also be referred to as PE.

In one example, for intrinsic atrial events (i.e. P-waves), the IACD is set equal to the interval from the beginning of the P-wave detected via a RA lead to the end of an atrial far field (AFF) event detected via the LV tip/ring pair. Note that an A pace test may also be performed. For paced atrial events (i.e. AERs), the IACD is set equal to the interval from the A-pulse to the end (or the peak) of the AFF event detected via the LV lead. Note, also, that the A sense test typically can be performed contemporaneously with the V sense test. That is, during the V sense test, the pacer/ICD detects P-waves on an A-IEGM channel sensed using an RA lead and/or delivers A-pulses to the RA using the RA lead. P-waves may be detected during a contemporaneous A sense test. A-pulses may be delivered during a contemporaneous A pace test. Hence, the V sense test may be performed at the same time as A sense/A pace tests to improve overall test efficiency. This is discussed in U.S. patent application Ser. No. 12/507,646, cited above, which is fully incorporated by reference herein.

At step 204, the device determines the preliminary IEGM-based "optimal" AV/PV and VV delays by calculating:

IEGM_PV=IACD+$\delta$−$\theta$ dPA=AR−PR

IEGM_AV=PV+dPA

IEGM_VV=$\alpha$($\Delta$+$\epsilon$) where $\epsilon$=IVCD_LR−IVCD_RL.

In these equations, $\delta$ is an offset set to 60 ms, if PR<100 ms, and set to 30 ms, if PR$\geq$100 ms. The ration coefficient $\alpha$ is a hard-coded or programmable value, which may be set to 0.5 in some examples. In one example, the PL correction ($\theta$) can be determined as follows. IEGM_VV is calculated based on $\Delta$ and $\epsilon$. (That is, IEGM_VV is preferably calculated first, before IEGM_PV.) Then, if IEGM_VV>0, a time delay ($PL_{LV}$) is measured from pacing pulse until the peak of the resulting LV evoked response. A baseline value is then subtracted from $PL_{LV}$ to yield $\theta$. Conversely, if IEGM_VV<0, a time delay ($PL_{RV}$) is measured from a V-pulse until the peak of the resulting RV evoked response. The baseline value is then subtracted from $PL_{RV}$ to yield $\theta$. In either case, the baseline value can be within a range of values such as 60 ms-80 ms and can be set to, e.g., 70 ms. See, again, U.S. patent application Ser. No. 12/132,563, which describes the determination and use of the PL correction value $\theta$. Insofar as the term "dPA" is concerned, in the above example, dPA is set to AR−PR. In other examples, dPA is a preset value set, for example, to 50 ms. In still other examples, dPA can be set based on atrial pacing latency. That is, IEGM_AV can be derived by measuring or detecting the end of a paced P-wave.

At step 206, the device then determines a range of values for performing a set of "full grid" pace tests by using the IEGM_AV and IEGM_VV values as starting points, such as by performing a 4×4 test using:

IEGM_AV±20 ms; IEGM_AV±40 ms

IEGM_VV±20 ms; IEGM_VV±40 ms or more generally:

IEGM_AV±A ms; IEGM_AV±2A ms

IEGM_VV±A ms; IEGM_VV±2A ms where A is a grid spacing value selected by the device or preprogrammed therein. Note that, by "full grid," it is meant that the device tests each combination of values within the defined grid range subject to the specified grid spacing. In the above example, the grid spacing is 20 ms and the test range is ±40 ms, yielding a 4×4 test. These are merely exemplary values. Both the grid spacing (20 ms) and the grid range (±40 ms) can be set to different values in other embodiments, yielding tests with more or fewer values (e.g. N×N tests or N×M tests, where N and M can be set to any suitable value.)

At step 208, for each combination of AV/VV delays within the full grid search pattern, the device delivers biventricular pacing pulses while measuring SVC coil-can impedance (Z) or other suitable Z vector values to determine values for Zmax and/or dZ/dtmax (using, e.g., 8-16 paced beats at each delay setting.) Zmax refers to the peak impedance within a given cardiac cycle; whereas dZ/dtmax refers to the peak rate of change of impedance (i.e. the greatest slope of Z), again within a given cardiac cycle. In one example, for each paced beat, the device measures Zmax and/or dZ/dtmax and then averages the values over the number of paced beats (e.g. 8-16.)

The impedance measurements can be obtained by transmitting electrical current between a pair of electrodes and subsequently measuring the voltage between the same or another pair of electrodes. The impedance may be calculated as the ratio of the measured voltage to the transmitted current. In some examples, a tri-phasic impedance pulse waveform is employed to sense the impedance signal. The tri-phasic waveform is a frequency-rich, low energy waveform that provides a net-zero charge and a net-zero voltage. An exemplary tri-phasic pulse waveform is described in detail in U.S. patent application Ser. No. 11/558,194, of Panescu et al., filed Nov. 9, 2006, (pending) entitled "Closed-Loop Adaptive Adjustment of Pacing Therapy based on Cardiogenic Impedance Signals Detected by an Implantable Medical Device." As noted above, although impedance is used in the examples described herein, other generally equivalent electrical values or parameters can instead be used, where appropriate, such as immittance, conductance, or admittance, and those skilled in the art can readily convert among the various values.

At step 210, the device determines values (AV_Z, VV_Z) for AV/VV that maximize either Zmax and/or dZ/dtmax for use as "adjusted" optimal biventricular pacing delays, then delivers CRT pacing accordingly to gain the benefit of the SVC coil-can Z-based optimization to achieve improved cardiac output or stroke volume within the patient (or to achieve other goals.) As explained above, it is believed that pacing delay values that generally improve Zmax and/or dZ/dtmax also serve to generally improve LV dP/dtmax and likewise serve to generally improve cardiac output and stroke volume. As also noted above, by employing IEGM_AV and IEGM_VV as starting values for a Z-based optimization, the total number of combinations of delay AV/VV values that need to be tested while measuring impedance can be reduced significantly as compared to grid search schemes that might otherwise test all permissible AV/VV delays.

As shown in FIG. 4, the overall procedure may be repeated to re-adjust the values of AV_Z and VV_Z by repeating the optimization procedures. This can be done periodically or on demand, as triggered by changes within the patient (such as detection of progression of heart failure.) In this manner, the procedure can address and respond to any changing characteristics of the heart of the patient or to changes due to medications so as to keep the values at or near optimal values.

Thus, FIG. 4 illustrates an exemplary technique for determining optimal or preferred values for AV/PV and VV pacing delays. As already noted and described, the PV delays are optimized based on the IEGM but are not further optimized based on Z. It should be understood that these pacing delay values—and all other "optimal" values discussed herein—are not necessarily truly optimal in any particular quantifiable sense. As can be appreciated, what constitutes a truly "optimal" value depends on the criteria used for judging the resulting performance, which can be subjective in the minds of some clinicians. The values for AV and VV set using this technique represent at least preferred values for use in pacing. Clinicians may choose to adjust these values via device programming for particular patients, at their discretion.

Figure 5:
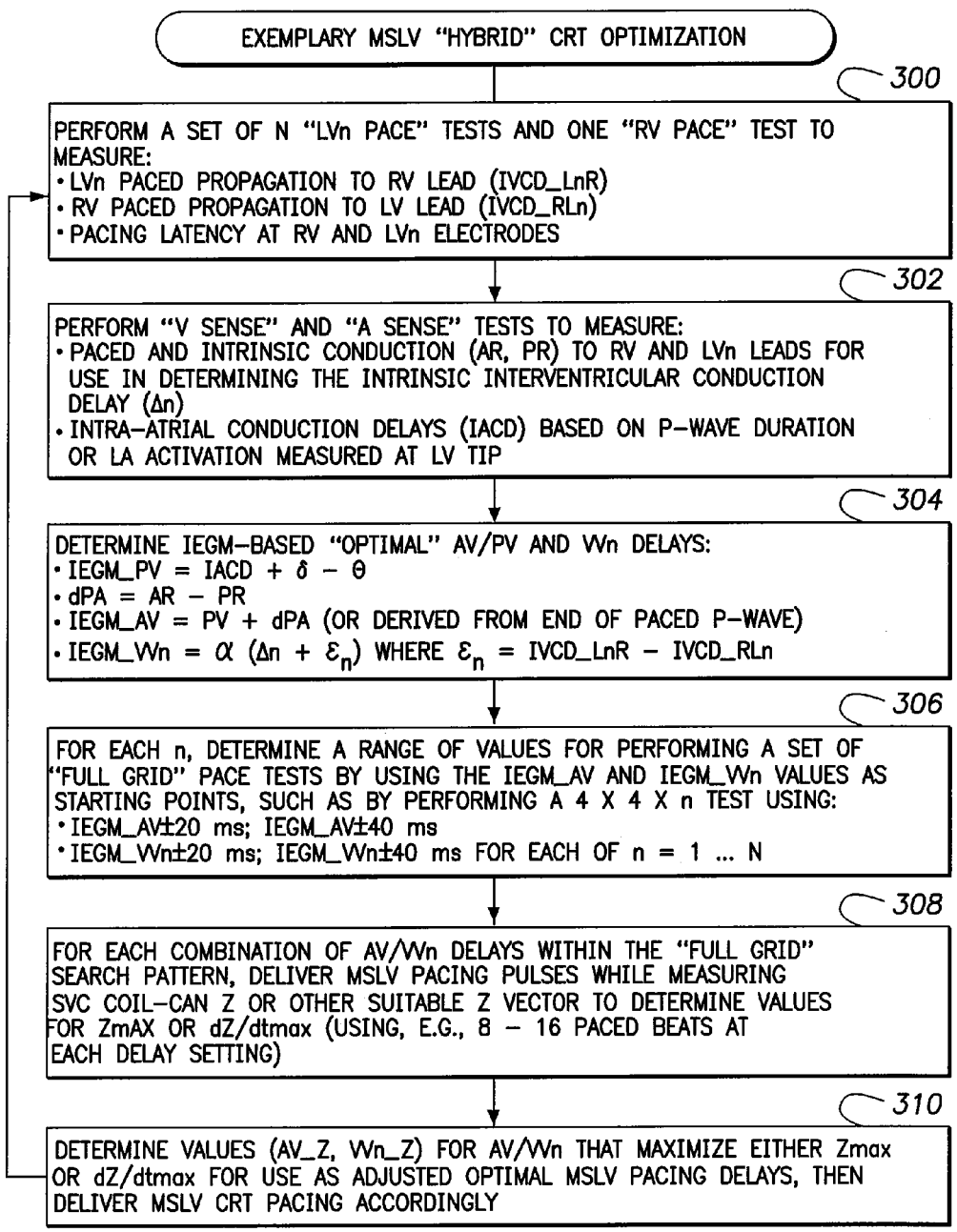
FIG. 5 illustrates an exemplary MSLV implementation of the hybrid technique of FIG. 3.

Turning now to FIG. 5, a corresponding technique for use with MSLV pacing is illustrated. Many of the steps of this technique are the same or similar to those of FIG. 4 and hence will not be described again in detail. Briefly, at step 300, the device performs a set of N "LVn pace" tests and one "RV pace" test to measure: (a) LVn paced propagation to RV lead (IVCD_LnR); (b) RV paced propagation to LV lead (IVCD_RLn); and (3) pacing latency at RV and LVn electrodes. In this regard, techniques for reducing the total number of LV and RV pace tests for use with MSLV leads are preferably exploited, which are described in U.S. patent application Ser. No. 12/507,646, cited and incorporated by reference above. With these techniques, only a single RV pace test is performed along with a set of N LVn pace tests so as to reduce total test time.

At step 302, the device performs "V sense" and "A sense" tests to measure: (a) paced and intrinsic conduction (AR, PR) to RV and LVn leads for use in determining $\Delta n$ and (b) the IACD based on P-wave duration or LA activation measured at the LV tip. At step 304, the device determines the preliminary IEGM-based "optimal" AV/PV and VVn delays by calculating:

IEGM_PV=IACD+$\delta$−$\theta$ dPA=AR−PR

IEGM_AV=PV+dPA

IEGM_VVn=0.5 ($\Delta n$+$\epsilon n$) where $\epsilon n$=IVCD_LnR−IVCD_RLn.

In these equations, $\delta$ is again an offset that may be set to 60 ms, if PR<100 ms, and set to 30 ms, if PR≥100 ms. A single PL correction ($\theta$) can be determined based on the latency to the LV tip or, in some examples, PL correction terms can be separately determined for each of the N electrodes of the LV lead, with the above-listed equations adjusted accordingly. As already noted, IEGM_AV can instead be derived by measuring or detecting the end of a paced P-wave.

At step 306, the device then determines a range of values for performing a set of N full grid pace tests by using the IEGM_AV and IEGM_VVn values as starting points, such as by performing a 4×4×N test using:

IEGM_AV±20 ms; IEGM_AV±40 ms

IEGM_VVn±20 ms; IEGM_VVn±40 ms for each value of n. As discussed above, both the grid spacing (20 ms) and the grid range (±40 ms) can be set to different values in other embodiments.

At step 308, for each combination of AV/VVn delays within the full grid search pattern, the device delivers MSLV pacing pulses while measuring SVC coil-can Z or other suitable Z vector values to determine values for Zmax and/or dZ/dtmax (again using, e.g., 8-16 paced beats at each delay setting.) At step 310, the device determines values (AV_Z, VVn_Z) for AV/VVn that maximize either Zmax and/or dZ/dtmax for use as adjusted optimal MSLV pacing delays, then delivers CRT pacing using the MSLV lead to gain the benefit of the Z-based optimization. By employing a search centered on the IEGM_AV and IEGM_VVn values, the number of combinations of AV/VVn values that need to be tested while measuring impedance can be reduced significantly as compared to grid search schemes that might otherwise test all permissible AV/VVn delays. As with the preceding embodiment, the overall procedure may be repeated to re-adjust the values of AV_Z and VV_Z by repeating the optimization procedures, periodically or on demand. This MSLV technique can also be applied to optimizing PV pacing delays based on IEGM values.

Note that, when MSLV is delivered, the choice of the particular LV electrode or electrodes for use in pacing may be made based on various considerations. See, for example, the considerations set forth in U.S. patent application No. 11/416,922, issued as U.S. Pat. No. 7,787,951, of Min et al., filed May 2, 2006, entitled "System and Method for Determining Optimal Pacing Stimulation Sites Based on ECG Information." Within some patients, combinations of two or more LV electrodes may be used to deliver ventricular pacing pulses. See, for example, U.S. patent application No. 11/749,662, (pending) filed May 16, 2007, of Ryu et al., entitled "Adaptive Single Site and Multi-Site Ventricular Pacing." Also, special techniques may be used to perform V sense, RV pace and LV pace tests during atrial fibrillation (AF.) See, for example, U.S. patent application No. 12/507,679, issued as U.S. Pat. No. 8,396,551, of Min, filed Jul. 22, 2009, and entitled "Systems and Methods for Optimizing Ventricular Pacing Delays during Atrial Fibrillation."

Note also that the specific IEGM-based optimization procedures listed in FIGS. 4 and 5 (such as those set forth in blocks 300, 302 and 304 of FIG. 5 for determining IEGM_AV and IEGM_VVn) are merely exemplary and may not be optimal. As an alternative, see the IEGM_AV and IEGM_VVn optimization techniques set forth in Ryu et al. (Ser. No. 11/749,662) (pending), and in the above-cited "multi-site pacing" applications of Min et al. (Ser. No. 12/507,646 (issued as U.S. Pat. No. 8,265,755), Ser. No. 12/639,881 (pending), and Ser. No. 12/604,280 (issued as U.S. Pat. No. 8,145,311)).

Direct Optimization Techniques Using IEGM and Z Parameters

Figure 6:
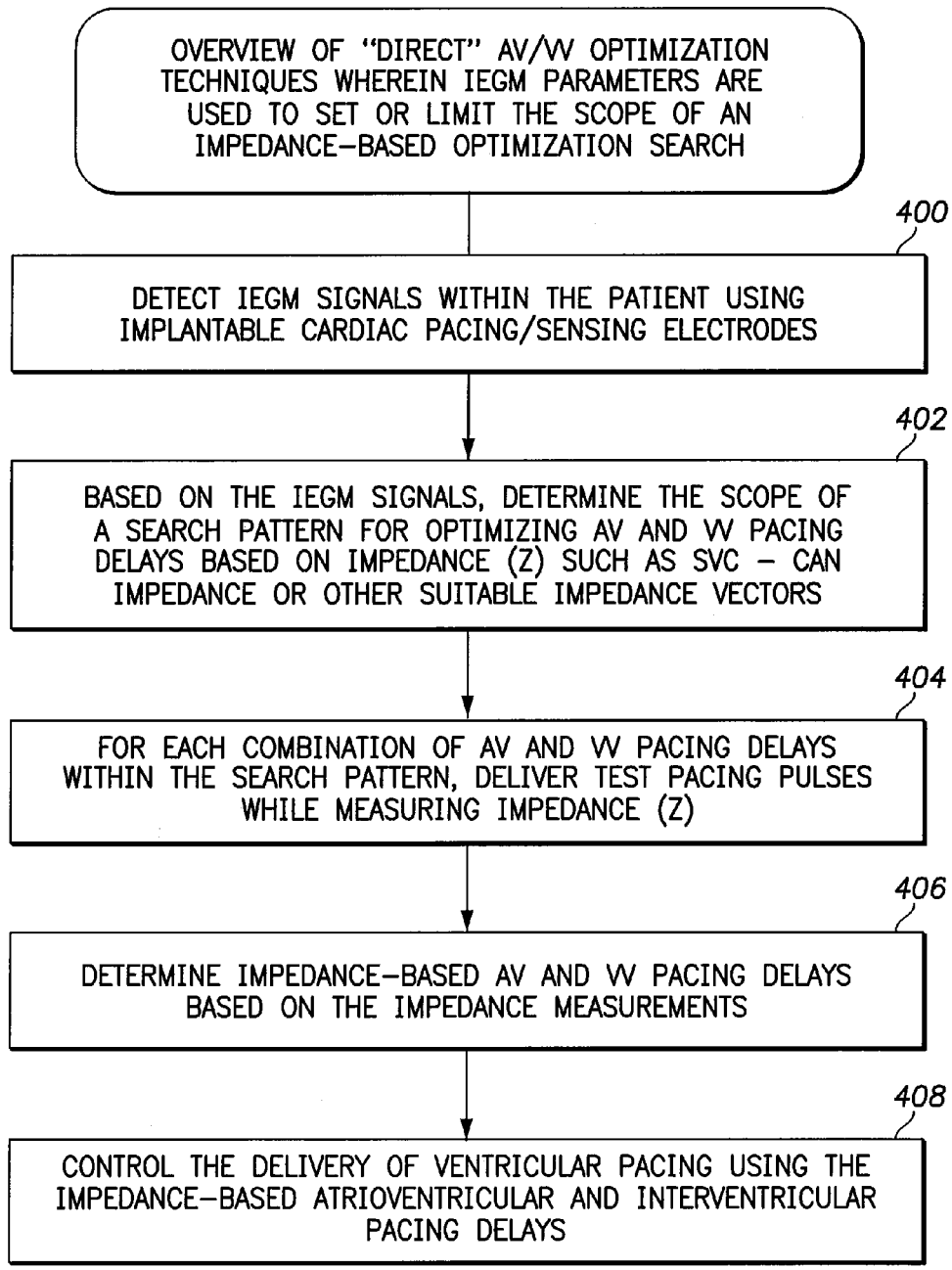
FIG. 6 provides an overview of the direct optimization techniques that may be performed by the systems of FIGS. 1 and 2, wherein IEGM signals are used to set or limit the search boundaries for subsequent Z-based optimization.

FIG. 6 broadly summarizes the direct technique wherein IEGM parameters are assessed for the purposes of setting or limiting the scope of a subsequent impedance-based optimization search. Beginning at step 400, the pacer/ICD detects IEGM signals within the patient using implantable cardiac pacing/sensing electrodes. Then, at step 402, based on the IEGM signals the device determines the scope of a search pattern for optimizing AV and VV pacing delays based impedance (Z) such as SVC—can impedance or other suitable impedance vectors. As will be explained, this can involve limiting the scope of a full grid optimization search to particular ranges of values so as to make the search more efficient. At step 404, for each combination of AV and VV pacing delays within the search pattern, the device delivers test pacing pulses while measuring impedance, such as by using SVC coil-can vector. At step 406, the device determines impedance-based AV and VV pacing delays (AV_Z, VV_Z) based on the impedance measurements. At step 408, the device then delivers ventricular pacing using the impedance-optimized pacing delays (AV_Z/VV_Z), such as by delivering CRT using those delays. In this manner, IEGM-based parameters are used to limit or refine the scope of a Z-based AV/VV optimization search to render the overall optimization procedure more efficient. This technique is referred to as a "direct" technique because the procedure proceeds directly to the Z-based optimization without first performing an IEGM-based (QuickOpt) optimization.

Figure 7:
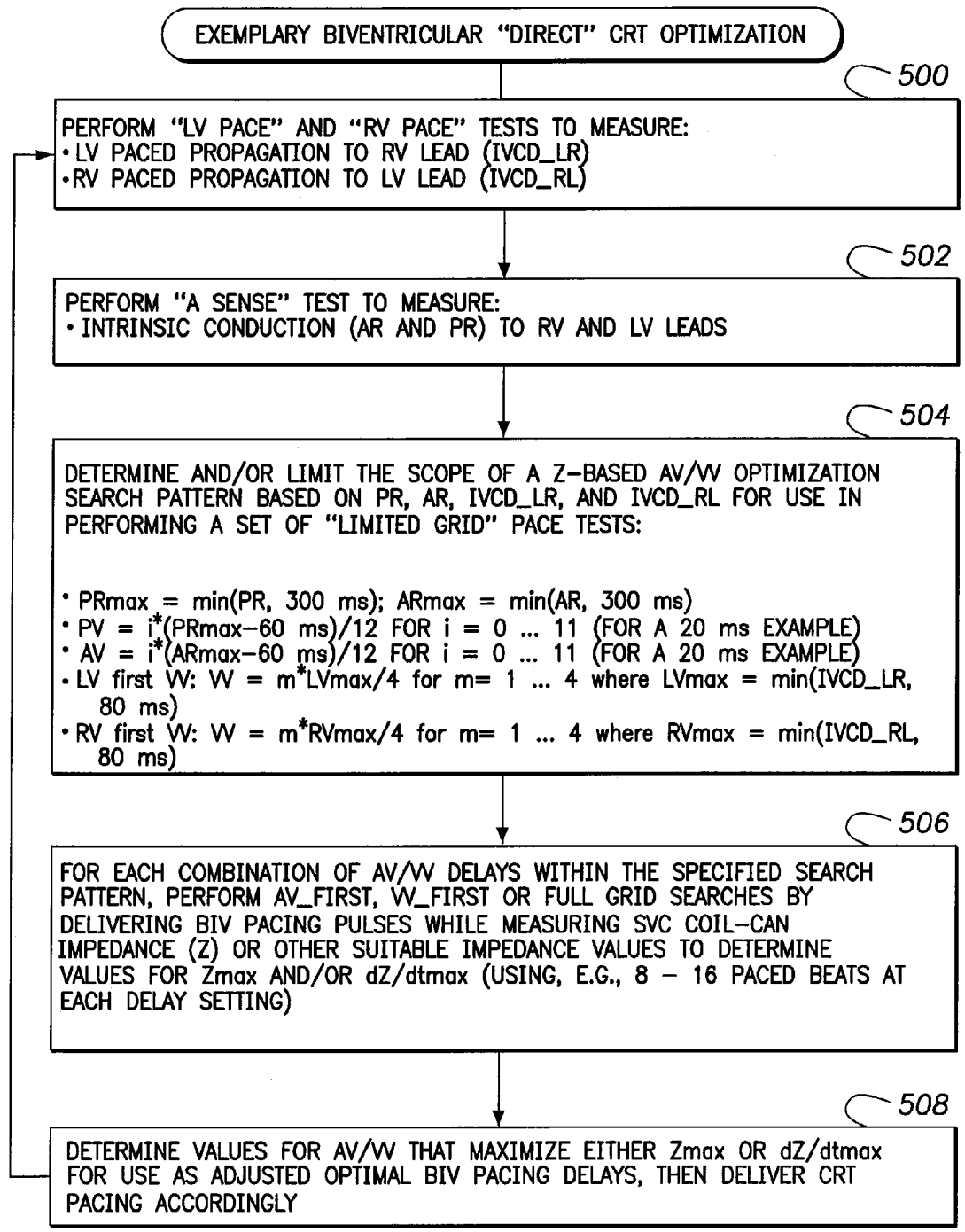
FIG. 7 illustrates an exemplary biventricular implementation of the direct technique of FIG. 6.

FIG. 7 provides a more detailed example of the direct technique. Some of steps are the same or similar to those already described in connection with the preceding figures and hence will not be described again in detail. Beginning at step 500, the device performs "LV pace" and "RV pace" tests to measure: (a) LV paced propagation to RV lead (IVCD_LR) and (b) RV paced propagation to LV lead (IVCD_RL). At step 502, the device performs "V sense" and "A sense" tests to measure: paced and intrinsic conduction (AR, PR) to RV and LV leads. (Additional parameters such as pacing latency can also be detected at step 500 and 502, though not needed for the procedure of FIG. 7.)

At step 504, the device determines the scope of a Z-based AV/VV optimization search pattern based on PR, AR, IVCD_LR, AND IVCD_RL for use in performing a set of "limited grid" pace tests. In one example where increments of 20 ms are used, this is achieved using:

PRmax=min(PR,300 ms); ARmax=min(AR,300 ms)

PV=i*(PRmax−60 ms)/12 for i=0 . . . 11 (for a 20 ms example)

AV=i*(ARmax−60 ms)/12 for i=0 . . . 11 (for a 20 ms example)

LV first VV:VV=m*LVmax/4 for m=1 . . . 4 where LVmax=min(IVCD_LR,80 ms)

RV first VV:VV=m*RVmax/4 for m=1 . . . 4 where RVmax=min(IVCD_RL,80 ms)

More generally, PRmax=min(PR, Y) and ARmax=min(AR, Y); wherein Y is a predetermined value, which may be set to 300 ms. LVmax=min(LV pace, Z) and RVmax=min(RV pace, Z) where Z is a predetermined value that may be set to 60 ms.

Hence, the values for PR, AR, IVCD_LR, AND IVCD_RL derived from the IEGM are used to limit the scope of the Z-based optimization search, which might otherwise include AV/VV values that exceed the bounds established by these formulae. Note that, in this particular example, it is assumed that the device has an allowed range of VV from −80 ms to 80 ms. There is no need to test VV>IVCD_LR or VV<IVCD_RL; hence the aforementioned LVmax and RVmax limitations. Also note that, in this 20 ms example, there are a total of twelve AV delays for testing and a total of nine VV delays for testing. In another example, where 40 ms increments are instead used:

PV=i*(PRmax−60 ms)/6 for i=0 . . . 5

AV=i*(ARmax−60 ms)/6 for i=0 . . . 5

In this 40 ms example, there are a total of six AV delays for testing.

At step 506, for each combination of AV/VV delays within the specified search pattern (i.e. within the search pattern as limited by the constraints specified in step 504), the device performs a set of AV_first, VV_first or "full grid" searches by delivering biventricular pacing pulses while measuring SVC coil-can impedance (Z) or other suitable impedance values to determine values for Zmax and/or dZ/dtmax (using, e.g., 8-16 paced beats at each delay setting.) More specifically:

AV first: VV=0 (fixed); vary the AV delays to find the optimal AV, then use optimal AV to vary VV delays for optimal VV;

VV first: AV delay is fixed such as 60 ms; VV delays are varied to find the optimal VV, then use optimal VV to vary AV delays;

Full grid: test for all the combination of AV and VV delays.

At step 508, the device determines values (AV_Z, VV_Z) for AV/VV that maximize either Zmax and/or dZ/dtmax for use as optimal biventricular pacing delays, then delivers CRT pacing accordingly. As with the preceding embodiments, the overall procedure may be repeated within a closed loop to re-adjust the values of AV_Z and VV_Z (and Z_PV if it is also calculated.) Note that corresponding techniques to those of FIG. 7 can be applied for an MSLV embodiment, rather than a biventricular embodiment. See, for example, the MSLV descriptions for FIG. 5.

Although primarily described with respect to examples having a pacer/ICD, other implantable medical devices may be equipped to exploit the techniques described herein such as CRT devices and CRT-D devices. For the sake of completeness, an exemplary pacer/ICD will now be described, which includes components for performing the functions and steps already described.

Exemplary Pacer/ICD

Figure 8:
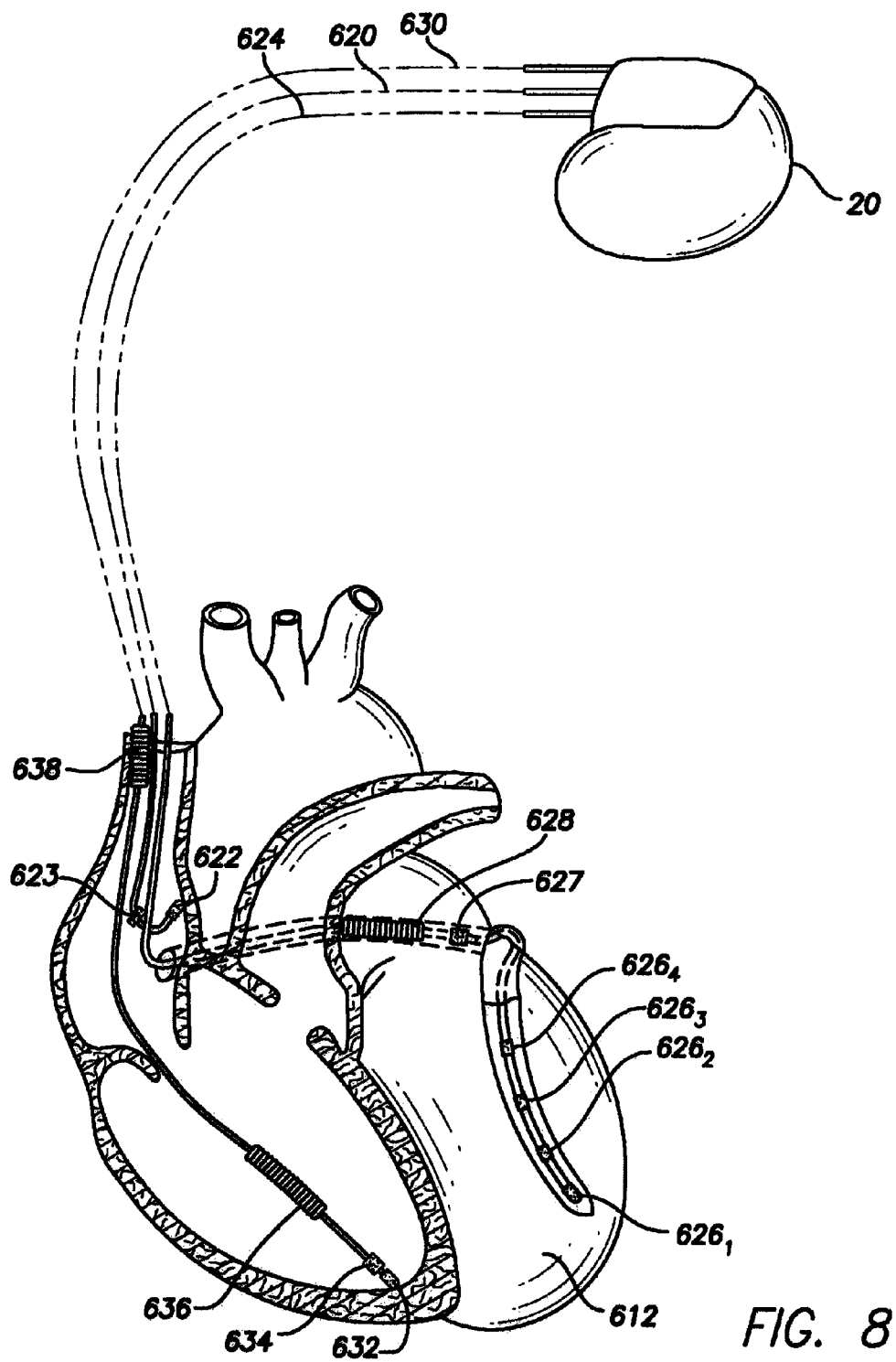
FIG. 8 is a simplified, partly cutaway view, illustrating the pacer/ICD of FIG. 2 along with at set of leads implanted into the heart of the patient.
Figure 9:
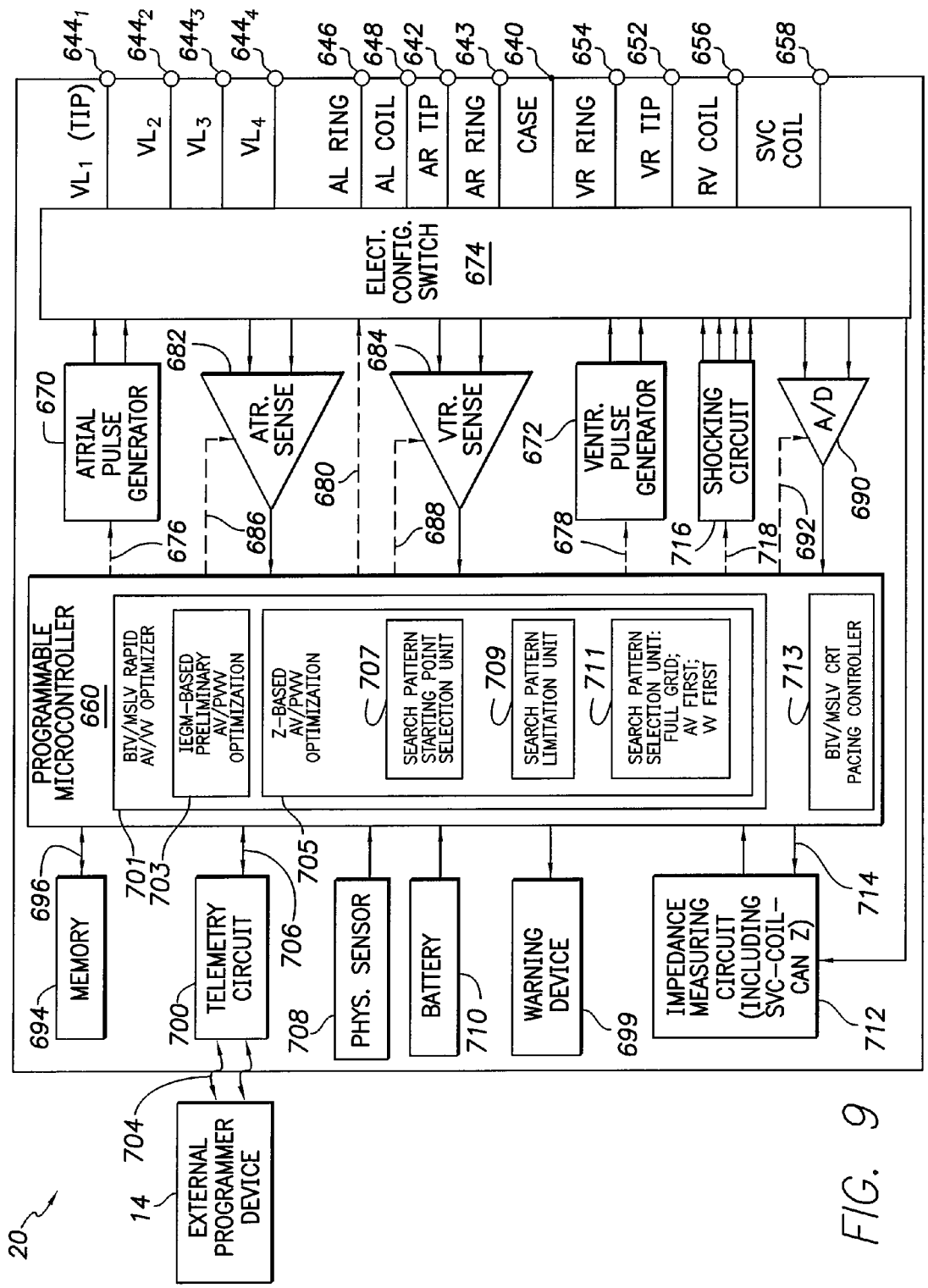
FIG. 9 is a functional block diagram of the pacer/ICD of FIG. 8, illustrating basic circuit elements that provide cardioversion, defibrillation and/or pacing stimulation in the heart an particularly illustrating an on-board optimization system for performing the optimization techniques of FIGS. 3-7.

With reference to FIGS. 8 and 9, a description of an exemplary pacer/ICD will now be provided. FIG. 8 provides a simplified block diagram of the pacer/ICD, which is a dual-chamber stimulation device capable of treating both fast and slow arrhythmias with stimulation therapy, including cardioversion, defibrillation, and pacing stimulation, and also capable of setting and using AV/VV pacing delays, as discussed above. To provide other atrial chamber pacing stimulation and sensing, pacer/ICD 20 is shown in electrical communication with a heart 612 by way of a left atrial lead 620 having an atrial tip electrode 622 and an atrial ring electrode 623 implanted in the atrial appendage. Pacer/ICD 20 is also in electrical communication with the heart by way of a right ventricular lead 630 having, in this embodiment, a ventricular tip electrode 632, a right ventricular ring electrode 634, a right ventricular (RV) coil electrode 636, and a superior vena cava (SVC) coil electrode 638. Typically, the right ventricular lead 630 is transvenously inserted into the heart so as to place the RV coil electrode 636 in the right ventricular apex, and the SVC coil electrode 638 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 20 is coupled to a multi-pole LV lead 624 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary LV lead 624 is designed to receive atrial and ventricular cardiac signals and to deliver left ventricular pacing therapy using a set of four left ventricular electrodes $626_1$, $626_2$, $626_3$, and $626_4$ (thereby providing a quadra-pole lead), left atrial pacing therapy using at least a left atrial ring electrode 627, and shocking therapy using at least a left atrial coil electrode 628. The 626₁ LV electrode may also be referred to as a "tip" or "distal" LV electrode. The 626₄ LV electrode may also be referred to as a "proximal" LV electrode. In other examples, more or fewer LV electrodes are provided. Although only three leads are shown in FIG. 8, it should also be understood that additional leads (with one or more pacing, sensing and/or shocking electrodes) might be used and/or additional electrodes might be provided on the leads already shown, such as additional electrodes on the RV lead.

A simplified block diagram of internal components of pacer/ICD 20 is shown in FIG. 9. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The housing 640 for pacer/ICD 20, shown schematically in FIG. 9, is often referred to as the "can", "case" or "case electrode" and may be programmably selected to act as the return electrode for all "unipolar" modes. The housing 640 may further be used as a return electrode alone or in combination with one or more of the coil electrodes, 628, 636 and 638, for shocking purposes. The housing 640 further includes a connector (not shown) having a plurality of terminals, 642, 643, 644₁-644₄, 646, 648, 652, 654, 656 and 658 (shown schematically and, for convenience, the names of the electrodes to which they are connected are shown next to the terminals). As such, to achieve right atrial sensing and pacing, the connector includes at least a right atrial tip terminal (AR TIP) 642 adapted for connection to the atrial tip electrode 622 and a right atrial ring ($A_R$ RING) electrode 643 adapted for connection to right atrial ring electrode 623. To achieve left chamber sensing, pacing and shocking, the connector includes a left ventricular tip terminal ($VL_1$ TIP) 644₁ and additional LV electrode terminals 644₂-644₄ for the other LV electrodes of the quadra-pole LV lead.

The connector also includes a left atrial ring terminal ($A_L$ RING) 646 and a left atrial shocking terminal ($A_L$ COIL) 648, which are adapted for connection to the left atrial ring electrode 627 and the left atrial coil electrode 628, respectively. To support right chamber sensing, pacing and shocking, the connector further includes a right ventricular tip terminal ($V_R$ TIP) 652, a right ventricular ring terminal ($V_R$ RING) 654, a right ventricular shocking terminal ($V_R$ COIL) 656, and an SVC shocking terminal (SVC COIL) 658, which are adapted for connection to the right ventricular tip electrode 632, right ventricular ring electrode 634, the $V_R$ coil electrode 636, and the SVC coil electrode 638, respectively.

At the core of pacer/ICD 20 is a programmable microcontroller 660, which controls the various modes of stimulation therapy. As is well known in the art, the microcontroller 660 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 660 includes the ability to process or monitor input signals (data) as controlled by a program code stored in a designated block of memory. The details of the design and operation of the microcontroller 660 are not critical to the invention. Rather, any suitable microcontroller 660 may be used that carries out the functions described herein. The use of microprocessor-based control circuits for performing timing and data analysis functions are well known in the art.

As shown in FIG. 9, an atrial pulse generator 670 and a ventricular pulse generator 672 generate pacing stimulation pulses for delivery by the right atrial lead 620, the right ventricular lead 630, and/or the LV lead 624 via an electrode configuration switch 674. It is understood that in order to provide stimulation therapy in each of the four chambers of the heart, the atrial and ventricular pulse generators, 670 and 672, may include dedicated, independent pulse generators, multiplexed pulse generators or shared pulse generators. The pulse generators, 670 and 672, are controlled by the microcontroller 660 via appropriate control signals, 676 and 678, respectively, to trigger or inhibit the stimulation pulses.

The microcontroller 660 further includes timing control circuitry (not separately shown) used to control the timing of such stimulation pulses (e.g., pacing rate, AV delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 674 includes a plurality of switches for connecting the desired electrodes to the appropriate I/O circuits, thereby providing complete electrode programmability. Accordingly, the switch 674, in response to a control signal 680 from the microcontroller 660, determines the polarity of the stimulation pulses (e.g., unipolar, bipolar, combipolar, etc.) by selectively closing the appropriate combination of switches (not shown) as is known in the art. The switch also switches among the various LV electrodes.

Atrial sensing circuits 682 and ventricular sensing circuits 684 may also be selectively coupled to the right atrial lead 620, LV lead 624, and the right ventricular lead 630, through the switch 674 for detecting the presence of cardiac activity in each of the four chambers of the heart. Accordingly, the atrial (ATR. SENSE) and ventricular (VTR. SENSE) sensing circuits, 682 and 684, may include dedicated sense amplifiers, multiplexed amplifiers or shared amplifiers and may receive control signals 686 and 688 from the controller 660. The switch 674 determines the "sensing polarity" of the cardiac signal by selectively closing the appropriate switches, as is also known in the art. In this way, the clinician may program the sensing polarity independent of the stimulation polarity. Each sensing circuit, 682 and 684, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 20 to deal effectively with the difficult problem of sensing the low amplitude signal characteristics of atrial or ventricular fibrillation. The outputs of the atrial and ventricular sensing circuits, 682 and 684, are connected to the microcontroller 660 which, in turn, are able to trigger or inhibit the atrial and ventricular pulse generators, 670 and 672, respectively, in a demand fashion in response to the absence or presence of cardiac activity in the appropriate chambers of the heart.

For arrhythmia detection, pacer/ICD 20 utilizes the atrial and ventricular sensing circuits, 682 and 684, to sense cardiac signals to determine whether a rhythm is physiologic or pathologic. As used in this section "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 660 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 690. The data acquisition system 690_receives control signals 692 from microcontroller 660 and is configured to acquire intracardiac electrogram signals, convert the raw analog data into a digital signal, and store the digital signals for later processing and/or telemetric transmission to an external device 14. The data acquisition system 690 is coupled to the right atrial lead 620, the LV lead 624, and the right ventricular lead 630 through the switch 674 to sample cardiac signals across any pair of desired electrodes. The microcontroller 660 is further coupled to a memory 694 by a suitable data/address bus 696, wherein the programmable operating parameters used by the microcontroller 660 are stored and modified, as required, in order to customize the operation of pacer/ICD 20 to suit the needs of a particular patient. Such operating parameters define, for example, the amplitude or magnitude, pulse duration, electrode polarity, for both pacing pulses and impedance detection pulses (including the aforementioned SVC coil-can pulses) as well as pacing rate, sensitivity, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 20 may be non-invasively programmed into the memory 694 through a telemetry circuit 700 in telemetric communication with the external device 702, such as a programmer, transtelephonic transceiver or a diagnostic system analyzer. The telemetry circuit 700 is activated by the microcontroller by a control signal 706. The telemetry circuit 700 advantageously allows intracardiac electrograms and status information relating to the operation of pacer/ICD 20 (as contained in the microcontroller 660 or memory 694) to be sent to the external device 702 through an established communication link 704. Pacer/ICD 20 further includes an accelerometer or other physiologic sensor 708, commonly referred to as a "rate-responsive" sensor because it is typically used to adjust pacing stimulation rate according to the exercise state of the patient. However, the physiological sensor 708 may further be used to detect changes in cardiac output, changes in the physiological condition of the heart, or diurnal changes in activity (e.g., detecting sleep and wake states) and to detect arousal from sleep. Accordingly, the microcontroller 660 responds by adjusting the various pacing parameters (such as rate, AV delay, VV delay, etc.) at which the atrial and ventricular pulse generators, 670 and 672, generate stimulation pulses. While shown as being included within pacer/ICD 20, it is to be understood that the physiologic sensor 708 may also be external to pacer/ICD 20, yet still be implanted within or carried by the patient. A common type of rate responsive sensor is an activity sensor incorporating an accelerometer or a piezoelectric crystal, which is mounted within the housing 640 of pacer/ICD 20. Other types of physiologic sensors are also known, for example, sensors that sense the oxygen content of blood, respiration rate and/or minute ventilation, pH of blood, ventricular gradient, etc.

The pacer/ICD additionally includes a battery 710, which provides operating power to all of the circuits shown in FIG. 9. The battery 710 may vary depending on the capabilities of pacer/ICD 20. If the system only provides low voltage therapy, a lithium iodine or lithium copper fluoride cell typically may be utilized. For pacer/ICD 20, which employs shocking therapy, the battery 710 should be capable of operating at low current drains for long periods, and then be capable of providing high-current pulses (for capacitor charging) when the patient requires a shock pulse. The battery 710 should also have a predictable discharge characteristic so that elective replacement time can be detected. Accordingly, appropriate batteries are employed.

As further shown in FIG. 9, pacer/ICD 20 has an impedance measuring circuit 712, which is enabled by the microcontroller 660 via a control signal 714. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 712 is advantageously coupled to the switch 674 so that any desired electrode may be used.

In the case where pacer/ICD 20 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 660 further controls a shocking circuit 716 by way of a control signal 718. The shocking circuit 716 generates shocking pulses of low (up to 0.5 joules), moderate (0.5-10 joules) or high energy (11 to 40 joules or more), as controlled by the microcontroller 660. Such shocking pulses are applied to the heart of the patient through at least two shocking electrodes, and as shown in this embodiment, selected from the left atrial coil electrode 628, the RV coil electrode 636, and/or the SVC coil electrode 638. The housing 640 may act as an active electrode in combination with the RV electrode 636, or as part of a split electrical vector using the SVC coil electrode 638 or the left atrial coil electrode 628 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 7-40 joules), delivered asynchronously (since R-waves may be too disorganized), and pertaining exclusively to the treatment of fibrillation. Accordingly, the microcontroller 660 is capable of controlling the synchronous or asynchronous delivery of the shocking pulses.

Insofar as ventricular pacing optimization is concerned, the microcontroller includes a biventricular/MSLV rapid VV optimizer 701 operative to perform or control the techniques of FIGS. 3-7, described above. Optimizer 701 includes an IEGM-based preliminary AV/PV/VV optimization system 703 operative to determine preliminary IEGM-based AV/PV/VV pacing delays using IEGM signals detected via the various sense amplifiers and A/D circuits, such as by exploiting the aforementioned QuickOpt techniques. Optimizer 701 also includes a Z-based AV/VV optimization system 705 operative to determine impedance-based AV/VV pacing delays based on SVC-can impedance signals or other suitable impedance signals. Z-based optimization system 705 includes a search pattern starting point selection unit 707 for setting the scope of an impedance-based optimization search based on the results of the IEGM-based optimization, in accordance with the techniques of FIGS. 3-5. Z-based optimization system 705 includes a search pattern limitation unit 709 for limiting the scope of an impedance-based optimization search, in accordance with the techniques of FIGS. 6-7. A search pattern selection unit 711 selects among the search patterns discussed above, namely full grid, AV first and VV first. A biventricular/MSLV CRT pacing controller 713 controls the delivery of CRT or other forms of pacing therapy using the impedance-based optimized AV and VV pacing delays (and optimized PV delays, if provided.) Diagnostic information pertaining to the optimization procedures, or other matters, can be stored in memory 694. An internal warning device 699 may be provided for generating perceptible warning signals to the patient via vibration, voltage or other methods.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

As noted, at least some of the techniques described herein can be performed by (or under the control of) an external device. For the sake of completeness, an exemplary device programmer will now be described, which includes components for controlling at least some of the functions and steps already described.

Exemplary External Programmer

Figure 10:
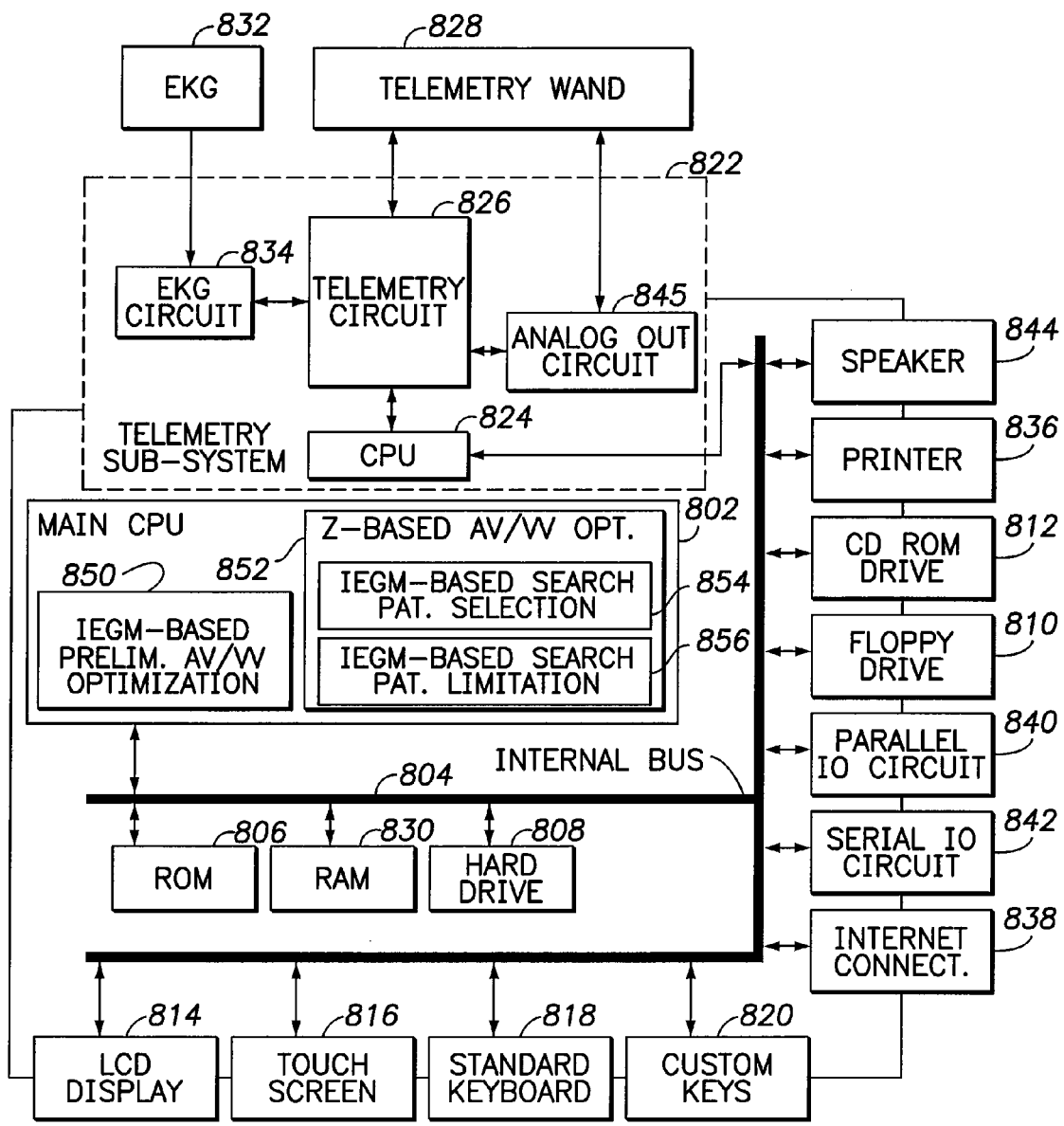
FIG. 10 is a functional block diagram illustrating components of the external device programmer of FIGS. 1 and 2 and particularly illustrating programmer-based optimization systems for controlling the optimization techniques of FIGS. 3-7.

FIG. 10 illustrates pertinent components of an external programmer 14 for use in programming the pacer/ICD of FIG. 9 and for performing the above-described optimization techniques. For the sake of completeness, other device programming functions are also described herein. Generally, the programmer permits a physician or other user to program the operation of the implanted device and to retrieve and display information received from the implanted device such as IEGM data and device diagnostic data. Additionally, the external programmer can be optionally equipped to receive and display electrocardiogram (EKG) data from separate external EKG leads that may be attached to the patient. Depending upon the specific programming of the external programmer, programmer 14 may also be capable of processing and analyzing data received from the implanted device and from the EKG leads to, for example, render preliminary diagnosis as to medical conditions of the patient or to the operations of the implanted device.

Now, considering the components of programmer 14, operations of the programmer are controlled by a CPU 802, which may be a generally programmable microprocessor or microcontroller or may be a dedicated processing device such as an application specific integrated circuit (ASIC) or the like. Software instructions to be performed by the CPU are accessed via an internal bus 804 from a read only memory (ROM) 806 and random access memory 830. Additional software may be accessed from a hard drive 808, floppy drive 810, and CD ROM drive 812, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 814 or other suitable computer display device. To this end, the CPU may, for example, display a menu of specific programmable parameters of the implanted device to be programmed or may display a menu of types of diagnostic data to be retrieved and displayed. In response thereto, the physician enters various commands via either a touch screen 816 overlaid on the LCD display or through a standard keyboard 818 supplemented by additional custom keys 820, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

Once all pacing leads are mounted and the pacing device is implanted, the various parameters are programmed. Typically, the physician initially controls the programmer 14 to retrieve data stored within any implanted devices and to also retrieve EKG data from EKG leads, if any, coupled to the patient. To this end, CPU 802 transmits appropriate signals to a telemetry subsystem 822, which provides components for directly interfacing with the implanted devices, and the EKG leads. Telemetry subsystem 822 includes its own separate CPU 824 for coordinating the operations of the telemetry subsystem. Main CPU 802 of programmer communicates with telemetry subsystem CPU 824 via internal bus 804. Telemetry subsystem additionally includes a telemetry circuit 826 connected to telemetry wand 828, which, in turn, receives and transmits signals electromagnetically from a telemetry unit of the implanted device. The telemetry wand is placed over the chest of the patient near the implanted device to permit reliable transmission of data between the telemetry wand and the implanted device. Herein, the telemetry subsystem is shown as also including an EKG circuit 834 for receiving surface EKG signals from a surface EKG system 832. In other implementations, the EKG circuit is not regarded as a portion of the telemetry subsystem but is regarded as a separate component.

Typically, at the beginning of the programming session, the external programming device controls the implanted devices via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Data retrieved from the pacer/ICD also includes the data stored within the recalibration database of the pacer/ICD (assuming the pacer/ICD is equipped to store that data.) Data retrieved from the implanted devices is stored by external programmer 14 either within a random access memory (RAM) 830, hard drive 808 or within a floppy diskette placed within floppy drive 810. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted devices is transferred to programmer 14, the implanted devices may be further controlled to transmit additional data in real time as it is detected by the implanted devices, such as additional IEGM data, lead impedance data, and the like. Additionally, or in the alternative, telemetry subsystem 822 receives EKG signals from EKG leads 832 via an EKG processing circuit 834. As with data retrieved from the implanted device itself, signals received from the EKG leads are stored within one or more of the storage devices of the external programmer. Typically, EKG leads output analog electrical signals representative of the EKG. Accordingly, EKG circuit 834 includes analog to digital conversion circuitry for converting the signals to digital data appropriate for further processing within the programmer. Depending upon the implementation, the EKG circuit may be configured to convert the analog signals into event record data for ease of processing along with the event record data retrieved from the implanted device. Typically, signals received from the EKG leads are received and processed in real time.

Thus, the programmer receives data both from the implanted devices and from optional external EKG leads. Data retrieved from the implanted devices includes parameters representative of the current programming state of the implanted devices. Under the control of the physician, the external programmer displays the current programmable parameters and permits the physician to reprogram the parameters. To this end, the physician enters appropriate commands via any of the aforementioned input devices and, under control of CPU 802, the programming commands are converted to specific programmable parameters for transmission to the implanted devices via telemetry wand 828 to thereby reprogram the implanted devices. Prior to reprogramming specific parameters, the physician may control the external programmer to display any or all of the data retrieved from the implanted devices or from the EKG leads, including displays of EKGs, IEGMs, and statistical patient information. Any or all of the information displayed by programmer may also be printed using a printer 836.

Additionally, CPU 802 also preferably includes components operative to perform or control the techniques of FIGS. 3-7, described above. An IEGM-based preliminary AV/VV optimization system 850 is operative to determine preliminary IEGM-based AV/VV pacing delays using IEGM signals detected by the implant device and transmitted to system 14. A Z-based AV/VV optimization system 852 is operative to determine impedance-based AV/VV pacing delays based on the SVC-can impedance signal. Z-based optimization system 852 includes an IEGM-based search pattern selection unit 854 for selecting the type of search and for setting the scope of an impedance-based optimization search based on the results of IEGM-based optimization, in accordance with the techniques of FIGS. 3-5. Z-based optimization system 852 also includes an IEGM-based search pattern limitation unit 856 for limiting the scope of an impedance-based optimization search, in accordance with the techniques of FIGS. 6-7. Pacing delay parameters and/or other pacing control information may then be transmitted to the pacer/ICD to program the device to perform pacing in accordance with the optimal or preferred AV/VV pacing delays (and PV delays, if also optimized.)

Programmer/monitor 14 also includes an internet connection component 838 to permit direct transmission of data to other programmers via the public switched telephone network (PSTN) or other interconnection line, such as a T1 line or fiber optic cable or via wireless systems. Depending upon the implementation, the internet connection may be connected directly to internal bus 804 may be connected to the internal bus via either a parallel port 840, a serial port 842 or other device. Other peripheral devices may be connected to the external programmer via parallel port 840 or a serial port 842 as well. Although one of each is shown, a plurality of input output (IO) ports might be provided. A speaker 844 is included for providing audible tones to the user, such as a warning beep in the event improper input is provided by the physician. Telemetry subsystem 822 additionally includes an analog output circuit 845 for controlling the transmission of analog output signals, such as IEGM signals output to an EKG machine or chart recorder.

With the programmer configured as shown, a physician or other user operating the external programmer is capable of retrieving, processing and displaying a wide range of information received from the implanted device and to reprogram the implanted device if needed. The descriptions provided herein with respect to FIG. 10 are intended merely to provide an overview of the operation of programmer and are not intended to describe in detail every feature of the hardware and software of the programmer and is not intended to provide an exhaustive list of the functions performed by the programmer.

In the following additional and/or alternative techniques are described wherein the order by which LV sites are paced is sorted and optimized and wherein circumstances where AV/PV pacing delays are longer than corresponding AR/PR conduction delays are addressed.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A method for controlling ventricular pacing within a patient for use by an implantable medical device, the method comprising:
  detecting intracardiac electrogram (IEGM) signals within the patient using electrodes;
  determining preliminary IEGM-based atrioventricular and interventricular pacing delays using the IEGM signals;
  detecting an impedance (Z) signal along a vector influenced by stroke volume within the patient;
  adjusting the preliminary IEGM-based atrioventricular and interventricular pacing delays based on the impedance signal to yield impedance-based atrioventricular and interventricular pacing delays;
  controlling the delivering of ventricular pacing using the impedance-based atrioventricular and interventricular pacing delays;
  wherein the device includes left ventricular (LV) and right ventricular (RV) leads and wherein detecting IEGM signals includes detecting LV IEGM and RV IEGM signals;
  wherein determining preliminary IEGM-based atrioventricular (AV) pacing delays comprises:
  determining intrinsic conduction delays (AR and PR) to the RV and LV leads, wherein AR and PR represent atrio-ventricular delays for stimulated and spontaneous atrial depolarization, respectively;
  determining an intra-atrial conduction delay (IACD);
  determining a preferred IEGM-based PV delay (IEGM PV) using IEGM PV=IACD+an offset, wherein PV delay represents a delay between an intrinsic P-wave and a ventricular stimulation pulse; and
  determining a preferred IEGM-based AV delay (IEGM AV) using IEGM AV=IEGM PV+AR−PR.

2. The method of claim 1 wherein the LV lead is a multi-site left ventricular (MSLV) lead and wherein detecting LV IEGM signals includes detecting LVn IEGM, where n represents an electrode of the MSLV lead.

3. The method of claim 2 wherein determining preliminary IEGM-based ventricular interconduction (VV) pacing delays includes, for each n:
  determining a set of LVn paced propagation delays to the RV lead (IVCD_LnR);

determining a set of RV paced propagation delays to LVn lead (IVCD_LnR);

determining a set of intrinsic interventricular conduction delays ($\Delta n$); and determining a set of preferred IEGM-based VV delays (IEGM_VVn) using IEGM_VVn=$\alpha(\Delta n+\epsilon n)$ where $\epsilon$ is a ratio factor and $\epsilon n$=IVCD_LnR-IVCD_RLn.

4. The method of claim 1 wherein all of the steps are performed by the implantable medical device.

5. The method of claim 1 wherein at least some of the steps are performed by an external device based on signals received from the implantable medical device.

* * * * *